(12) United States Patent
Ball et al.

(10) Patent No.: US 8,285,384 B2
(45) Date of Patent: Oct. 9, 2012

(54) IMPLANTABLE MEDICAL DEVICES WITH MULTIPLE TRANSDUCERS

(75) Inventors: Geoffrey Ball, Axams (AT); Marcus Schmidt, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 1101 days.

(21) Appl. No.: 11/654,917

(22) Filed: Jan. 17, 2007

(65) Prior Publication Data

US 2007/0282397 A1    Dec. 6, 2007

Related U.S. Application Data

(63) Continuation of application No. 10/660,283, filed on Sep. 10, 2003, now abandoned.

(60) Provisional application No. 60/409,394, filed on Sep. 10, 2002.

(51) Int. Cl.
*A61N 1/36* (2006.01)

(52) U.S. Cl. .............. 607/57; 607/137; 600/25

(58) Field of Classification Search .......... 600/25; 607/55–57, 136, 137
See application file for complete search history.

(56) References Cited

U.S. PATENT DOCUMENTS

| | | | |
|---|---|---|---|
| 4,532,930 A | 8/1985 | Crosby et al. | 607/57 |
| 5,176,620 A | 1/1993 | Gilman | |
| 5,897,486 A * | 4/1999 | Ball et al. | 600/25 |
| 6,074,422 A * | 6/2000 | Berrang et al. | 623/10 |
| 6,161,046 A * | 12/2000 | Maniglia et al. | 607/57 |
| 6,190,305 B1 | 2/2001 | Ball et al. | 600/25 |
| 6,198,971 B1 * | 3/2001 | Leysieffer | 607/55 |
| 6,231,604 B1 * | 5/2001 | von Ilberg | 623/10 |
| 6,259,951 B1 | 7/2001 | Kuzma et al. | |
| 6,421,569 B1 | 7/2002 | Treaba et al. | |
| 6,565,503 B2 | 5/2003 | Leysieffer et al. | 600/25 |
| 6,592,512 B2 | 7/2003 | Stockert et al. | 600/25 |
| 6,611,718 B2 | 8/2003 | Zilberman et al. | |
| 6,620,094 B2 | 9/2003 | Miller | 600/25 |
| 6,629,923 B2 | 10/2003 | Leysieffer | 600/25 |
| 6,697,674 B2 | 2/2004 | Leysieffer | 607/57 |
| 2001/0031996 A1 * | 10/2001 | Leysieffer | 607/57 |
| 2001/0049466 A1 * | 12/2001 | Leysieffer et al. | 600/25 |
| 2001/0056291 A1 * | 12/2001 | Zilberman et al. | 607/57 |
| 2002/0029070 A1 * | 3/2002 | Leysieffer et al. | 607/57 |
| 2002/0071581 A1 * | 6/2002 | Leysieffer et al. | 381/312 |

FOREIGN PATENT DOCUMENTS

| | | |
|---|---|---|
| EP | 0076069 | 9/1982 |
| EP | 0 076 069 | 4/1983 |
| WO | 95/01710 | 1/1995 |
| WO | WO 95/01710 | 1/1995 |
| WO | 00/69512 | 11/2000 |
| WO | WO 00/69512 | 11/2000 |

* cited by examiner

*Primary Examiner* — Carl H Layno
*Assistant Examiner* — Jessica Sarcione
(74) *Attorney, Agent, or Firm* — Sunstein Kann Murphy & Timbers LLP (57) ABSTRACT

Devices with both electrical and mechanical signal transducers can be used for improving sound perception by individuals with severe to profound hearing loss or tinnitus.

4 Claims, 5 Drawing Sheets

IMPLANTABLE MEDICAL DEVICES WITH MULTIPLE TRANSDUCERS

The present application is a Continuation of U.S. application Ser. No. 10/660,283, filed Sep. 10, 2003, now abandoned, which claims priority to U.S. Provisional Application Ser. No. 60/409,394, filed Sep. 10, 2002.

FIELD OF THE INVENTION

The present invention relates to implantable medical devices for improving sound perception by individuals with severe to profound hearing loss or tinnitus. In particular, the present invention provides methods and devices for stimulating structures of the ear via multiple signal transducers.

BACKGROUND OF THE INVENTION

Hearing impairment can be characterized according to its physiological source. There are two general categories of hearing impairment, conductive and sensorineural, although sometimes a combination of both may arise (mixed). Conductive hearing impairment results from diseases or disorders that limit the transmission of sound through the outer and/or middle ear. Conductive hearing impairment is often treated surgically with an implanted prosthesis to replace part or all of the ossicles. Sensorineural hearing impairment occurs in the inner ear and/or neural pathways and accounts for the vast majority of hearing impairment. In patients with sensorineural hearing impairment, the external and middle ear function normally. The sound vibrations are transmitted undisturbed through the eardrum and ossicles where fluid waves are created in the cochlea. However, because some of the delicate sensory hair cells inside the cochlea have degenerated or been damaged, the inner ear cannot detect the full intensity and quality of the sound. Acquired sensorineural hearing loss can occur as a result of aging or exposure to loud noise over a protracted period of time.

Hearing loss is quantified as borderline or slight, mild, moderate, severe, and profound, according to the volume of sounds that can be heard without amplification. Individuals with severe hearing loss are unable to hear sound below 70 dB and individuals with profound hearing loss are unable to hear sound below 91 dB. In practical terms, a person with severe hearing loss is incapable of hearing sounds softer than that of a busy street, while a person with profound hearing loss is incapable of hearing sounds softer than that of a subway. Without any type of assistance, normal conversation is not heard by individuals in either group. Over half a million Americans are suffering from severe to profound hearing loss (Mohr et al., 2000, Int. J. Technol. Assess Health Care, 16:1120-1135).

Tinnitus or ringing in the ears is another frequently debilitating auditory problem characterized by the perception of ringing, hissing, or other sound in the ears or head when no external sound is present. About 12 million Americans have severe enough tinnitus to seek medical attention, and about two million of these are seriously incapacitated by this condition. Untreated hearing impairments result in lost productivity, and increased medical and educational expenditures. Thus, apart from consequences to the individual, hearing loss is costly to society.

Traditional approaches to the management of sensorineural hearing impairment and tinnitus involve the use of hearing aids or cochlear implants. Hearing aids are commonly used to manage the mild to severe sensorineural hearing-impaired population. Cochlear implants are indicated for individuals with severe to profound hearing loss. Hearing aids are devices that acoustically amplify sound to increase the movement of the tympanic membrane and indirectly vibrate the ossicles. Cochlear implants electronically stimulate the inner ear through a series of electrodes implanted in the cochlea during a surgical procedure.

However, stimulation of structures of the ear only acoustically or electronically, is not sufficient to provide optimal hearing correction and is frequently accompanied by undesirable side effects. For instance, traditional hearing aids provide limited hearing assistance in the high frequency range, whereas, cochlear implants provide limited hearing assistance in the low frequency range. In addition, traditional hearing aids do not always produce clear natural sounds, and cochlear implants do not always correct and may even aggravate tinnitus.

Thus, there remains a need in the art for medical devices that provide hearing correction across the entire normal audio frequency range for individuals with severe to profound hearing loss or tinnitus. The present invention provides partially and fully implantable hearing devices that provide suitable stimulation to structures of the ear resulting in superior hearing correction.

SUMMARY OF THE INVENTION

The present invention relates to implantable medical devices for improving sound perception by individuals with severe to profound hearing loss or tinnitus. In particular, the present invention provides methods and devices for stimulating structures of the ear via multiple signal transducers.

The present invention provides devices for improving hearing in a subject, comprising: a transducer comprising a magnet and a coil disposed within and attached to a housing, the magnet producing a first magnetic field and the first coil producing a second magnetic field, the first and second magnetic fields interacting to cause vibrations of the housing, at least one electrode, a receiver, a means for conducting current between the receiver and the transducer, and a means for conducting current between the receiver and the at least one electrode. In preferred embodiments, the transducer is a floating mass transducer. In some embodiments, the transducer is configured for attachment to a subject's temporal bone. In other embodiments, the transducer is configured for attachment to a bone of a subject's ossicular chain. In further embodiments, the transducer is configured for attachment to a subject's round window. Also provided are embodiments, wherein the at least one electrode is configured for attachment to a subject's round window. In other embodiments, the at least one electrode is configured for attachment to an outer surface of a subject's round window. In further embodiments, the at least one electrode comprises a microelectrode array configured for insertion within a subject's cochlea. Also provided are embodiments, wherein the receiver is configured for implantation within a subject's mastoid bone. Some embodiments, the devices for improving hearing in a subject further comprise an audio processor comprising: a microphone, a circuit, a battery, and a coil, disposed within and attached to a housing.

The present invention also provides methods of improving hearing in a subject, comprising the steps of: providing a device comprising: i) a transducer comprising a magnet and a coil disposed within and attached to a housing, the magnet producing a first magnetic field and the first coil producing a second magnetic field, the first and second magnetic fields interacting to cause vibrations of the housing, ii) at least one electrode, iii) a receiver, and iv) a first pair of leads and a second pair of leads; surgically implanting the transducer in the middle ear of a subject, the at least one electrode in the inner ear of the subject and the receiver external to the middle ear; and conducting current from the receiver to the implanted transducer through the first pair of leads so as to cause the housing to vibrate, and conducting current from the receiver to the at least one implanted electrode through the second pair of leads, so as to transmit electrons to a structure of the inner ear. In some embodiments, the hearing impaired subject is selected from the group consisting of a subject with severe to profound hearing loss and a subject with tinnitus. In some preferred embodiments, the hearing impaired subject is capable of hearing sounds louder than 60 decibels at some but not all frequencies in the audible frequency range. Also provided are embodiments, wherein the surgically implanting comprises: creating a channel in the temporal bone of the subject; inserting the transducer through the channel into the middle ear; and inserting the at least one electrode through the channel into the inner ear. In some preferred embodiments, the surgically implanting further comprises securing the housing to an ossicle in the middle ear. In some embodiments, the surgically implanting further comprises securing the at least one electrode to the round window in the inner ear. In other embodiments, the surgically implanting further comprises securing the at least one electrode to an outer surface of the cochlea in the inner ear. In still further embodiments, the surgically implanting further comprises insertion of the at least one electrode within the cochlea in the inner ear. In some preferred embodiments, the surgically implanting further comprises replacement of the cochlear fluid. Also provided are embodiments, wherein the surgically implanting further comprises shaping a concave portion of the mastoid and subcutaneously placing the receiver in the concave portion.

Moreover, the present invention provides devices for improving hearing in a subject, comprising: a microphone, a battery, electronics, at least one electrical transducer suitable for transmission of an electric signal to a structure of a subject's inner ear, and at least one mechanical transducer suitable for transmission of a mechanical signal to a structure of a subject's middle ear. In some devices, the electronics comprise signal processing electronics, charging electronics, and system management electronics. In some embodiments, the microphone is disposed within and attached to a microphone housing and wherein leads extend from the microphone to a position outside the microphone housing. In further embodiments, the microphone is selected from the group consisting of an omnidirectional microphone and a bidirectional microphone. In some preferred embodiments, a protective cover is attached to the microphone, while in particularly preferred embodiments, the device further comprising an amplifier. Additionally, devices are provided wherein the battery is disposed within and attached to a battery housing and wherein leads extend from the battery to a position outside of the battery housing. In some embodiments, the device further comprises a means to signal low charge state of the battery. In other embodiments, the device further comprises external charge unit comprising a battery status indicator for detecting the charge state of the battery. Moreover, devices are provided wherein the electronics are disposed within and attached to an electronics housing. In preferred embodiments, the electronics comprise a telemetry block and a communications block. In some embodiments, the telemetry block is selected from the group consisting of a bidirectional telemetry block and a unidirectional telemetry block. Also provided are devices wherein the telemetry block and the communications block comprise a dual coil. Alternatively, devices are provided wherein the telemetry block and the communications block comprise at least two resonant coils. In some embodiments, the devices further comprise a magnet to facilitate alignment of the at least two resonant coils. In preferred embodiments, an alternating current signal is transmitted between the at least two resonant coils, an amplitude modulated signal is transmitted between the at least two resonant coils, or a base band signal is transmitted between the at least two resonant coils. In some embodiments, an alternating current signal in the audio frequency band is transmitted between the at least two resonant coils, while in other embodiments, an alternating current signal above 20,000 hertz is transmitted between the at least two resonant coils. In some particularly preferred embodiments, the microphone, the power supply, and the electronics, are attached to and disposed within a combined housing, and wherein the at least one electrical transducer and the at least one mechanical transducer are located external to the combined housing. In a subset of these embodiments, the combined housing is selected from the group consisting of a ceramic housing and a titanium housing. In some preferred embodiments, the combined housing is suitable for surgical implantation in a subject's mastoid bone. Also provided are devices wherein the mechanical transducer has a resonant frequency between 250 and 10,000 hertz.

Additionally, the present invention provides devices for improving hearing in a subject, comprising: a microphone, a battery, electronics, at least one electrical transducer (such as a cochlear implant) suitable for transmission of an electric signal to a structure of a subject's inner ear, and at least one mechanical transducer (such as a floating mass transducer) suitable for transmission of a mechanical signal to a structure of a subject's middle ear. Also provided by the present invention are devices that further comprise a means for storing subject data and device data. In preferred embodiments, the devices further comprise at least one set of leads, wherein the leads are selected from the group consisting of detachable leads and nondetachable leads. In some devices, the microphone is a directional microphone comprising at least two input transducers. Also in some devices, the electronics comprise signal processing electronics, charging electronics, and system management electronics. In some devices, the electrical transducer and the mechanical transducer comprise physically separate output channels that work along parallel paths. In other devices the output channels work along the same path in concert. In some devices the electrical transducer output channel and the mechanical transducer output channel are activated or inactivated independently. Also provided are devices where both transducer output channels are programmed using a universal external programming device. In some devices, the universal external programming device permits the programming of the signal processing and transducer output channels on a single platform. In preferred embodiments, the mechanical transducer is suitable for surgical implantation independently from surgical implantation of at least one of the electrical transducer, the microphone, the battery and the electronics. In some devices the at least one electrode is implanted to a depth within the cochlea of 20 millimeters or more, while in other devices the at least one electrode is implanted to a depth within the cochlea of less than 20 millimeters. Moreover, some devices are suitable for use in combination with an externally located FM audio broadcast system.

DESCRIPTION OF THE FIGURES

FIG. 1 shows pre and post medical implant audiograms for two hypothetical patients. Panels A and B provide pre and post audiograms for a patient with residual hearing in the low frequency range. Panels C and D provide pre and post audiograms for a patient with residual hearing in the high frequency range.

FIG. 2, Panels A, B and C, show several embodiments of a dual mode hearing device comprising mechanical stimulation in the form of a floating mass transducer positioned on the ossicular chain, and electric stimulation in the form of electrodes placed in or on the cochlea (e.g., cochlear implant) or round window.

FIG. 3 shows two embodiments of a dual mode hearing device comprising juxtaposed floating mass transducer and electrode(s). In Panel A, the stimulation means of the hearing device are implanted in the middle ear (e.g., the electrode is adjacent to the floating mass transducer housing which is attached to the surface of the round window). In Panel B, the stimulation means of the hearing device are implanted in the inner ear (e.g., the floating mass transducer is connected in series to several electrodes implanted in the cochlea).

FIG. 4, Panels A, B, and C, show several embodiments of the hearing device including both two and three stimulation modes (e.g., ultrasonic, mechanical, and electrical).

DESCRIPTION OF THE INVENTION

The present invention relates to implantable medical devices for improving sound perception by individuals with severe to profound hearing loss or tinnitus. In particular, the present invention provides methods and devices for stimulating structures of the ear via multiple signal transducers.

Treatment Population

The present invention provides implantable hearing devices comprising at least two transducers to provide hearing correction across the entire normal audio frequency range for individuals with severe or profound hearing loss or tinnitus. Individuals with residual hearing over one frequency range (e.g., 10-30 dB of useful dynamic range), but no or little hearing over a second frequency range are particularly good candidates for the hearing devices disclosed herein. Additionally, patients who have rejected standard cochlear implants due to medical or performance issues are anticipated to receive benefit from the multi-transducer hearing devices of the present invention.

In one embodiment, a floating mass transducer is used to provide hearing correction in the residual hearing frequency range, and a cochlear implant is used to provide hearing correction in the non-hearing frequency range. As shown in FIG. 1, Panels A and B, an individual with residual hearing in the low frequency range receives mechanical stimulation in the low frequency range and electrical stimulation in the high frequency range. Conversely, as shown in FIG. 1, Panels C and D, an individual with residual hearing in the high frequency range receives mechanical stimulation in the high frequency range and electronic stimulation in the low frequency range. For both patients, some frequencies receive mechanical as well as electronic stimulation.

Stimulation Modes

Mechanical stimulation is provided by the audio and/or ultrasonic floating mass transducer (FMT) component(s) of the hearing device. Briefly, the FMT is a transducer with a mass that vibrates in direct response to an external signal which corresponds to sound waves. The mass is mechanically coupled to a housing which is mountable on a vibratory structure of the ear. Thus, the mechanical vibration of the floating mass is transformed into a vibration of the vibratory structure of the ear (e.g., tympanic membrane, malleus, incus, and stapes, oval window, round window, and cochlea). Each of the vibratory structures of the ear vibrates to some degree when a person with normal hearing hears sound waves. However, hearing loss in a person may be evidenced by one or more vibratory structures vibrating less than normal or not at all. FMTs suitable for use as components of the present invention include but are not limited to those disclosed in U.S. Pat. No. 6,190,305, hereby incorporated by reference in its entirety.

Electric stimulation is provided by the coclear implant (CI) component of the hearing device. Briefly, the CI delivers electric signals to the cochlea which correspond to ambient sounds. As the cochlea is naturally partitioned into regions responsive to signals in a particular frequency range, an electrode array with a plurality of electrodes is utilized to deliver a cochlea stimulating signal within a preselected frequency range to the appropriate region. The electrical currents and electric fields from each electrode, which may be active simultaneously, stimulate the auditory nerve cells disposed in the modiolus of the cochlea. CIs suitable for use as components of the present invention include but are not limited to those disclosed in U.S. Pat. No. 6,421,569, incorporated herein.

Multiple Mode Devices

Figure 1A:
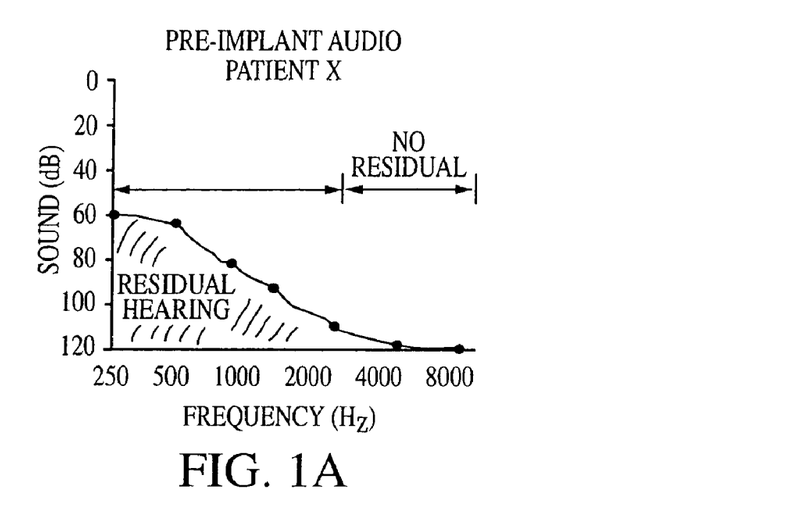
Figure 1B:
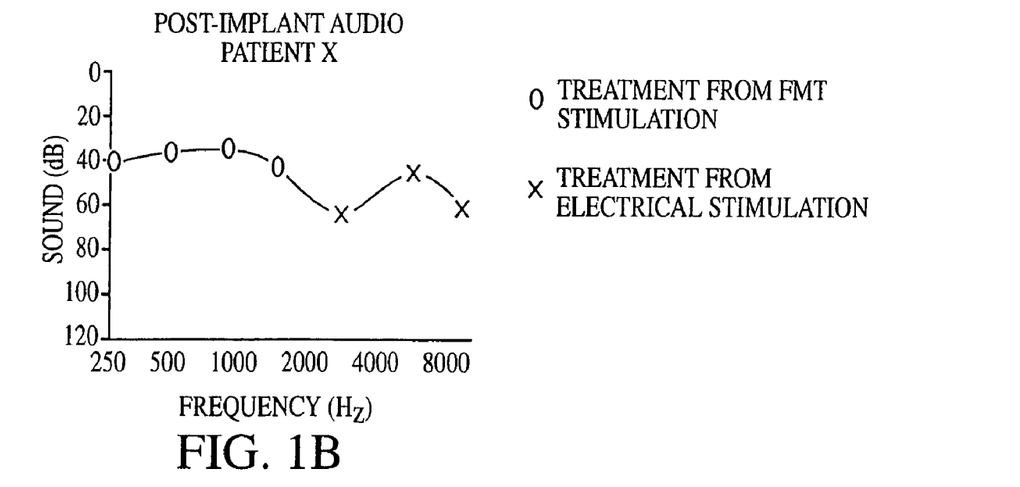
Figure 1C:
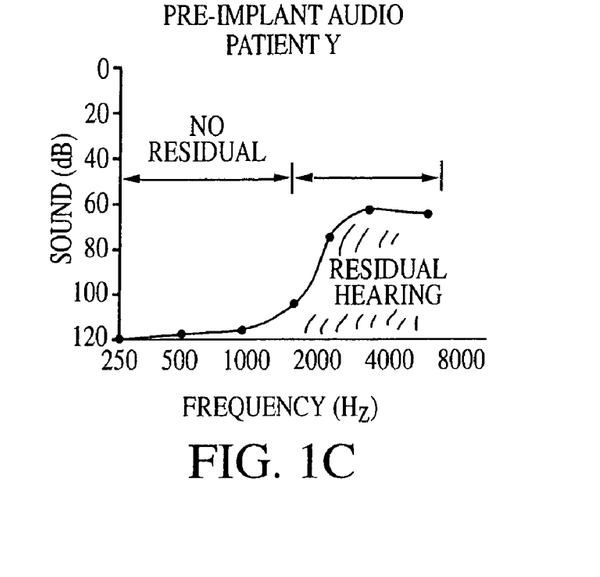
Figure 1D:
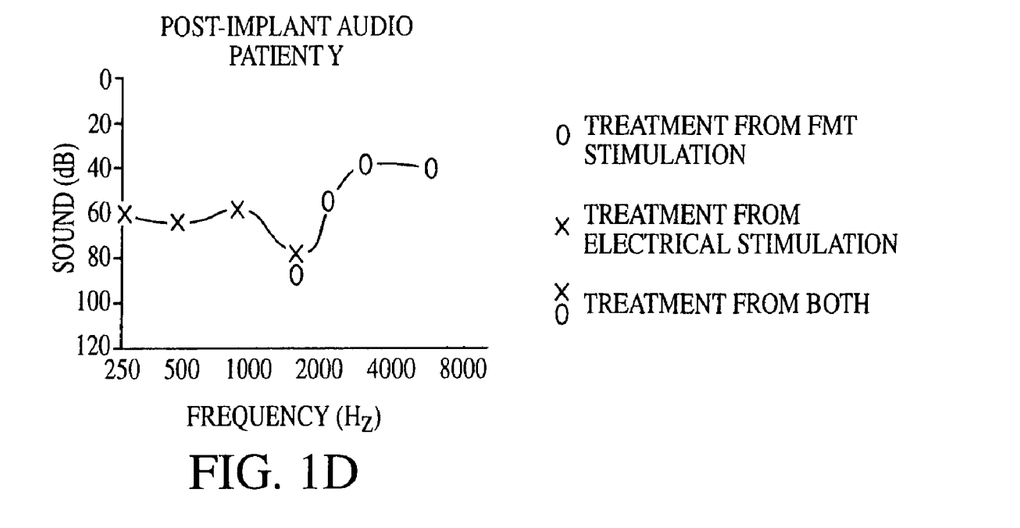
Figure 2A:
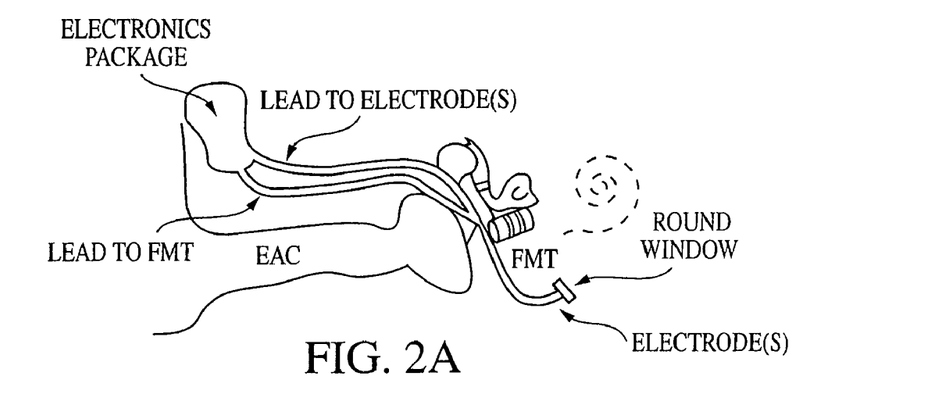
Figure 2B:
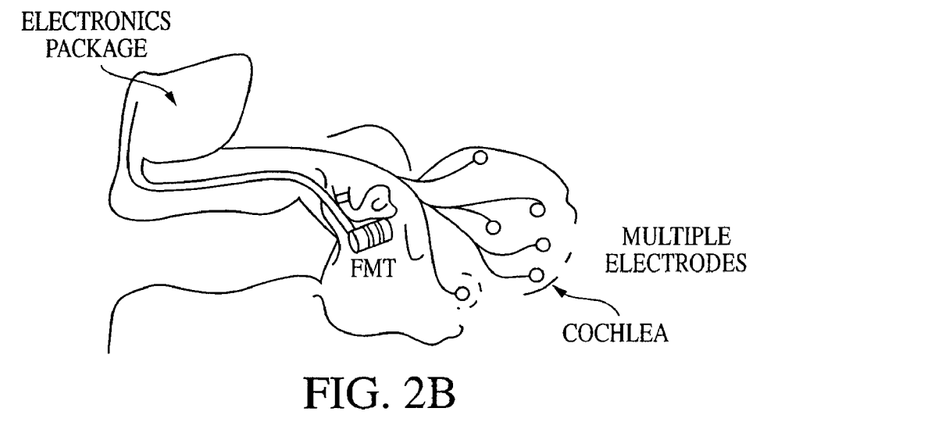
Figure 2C:
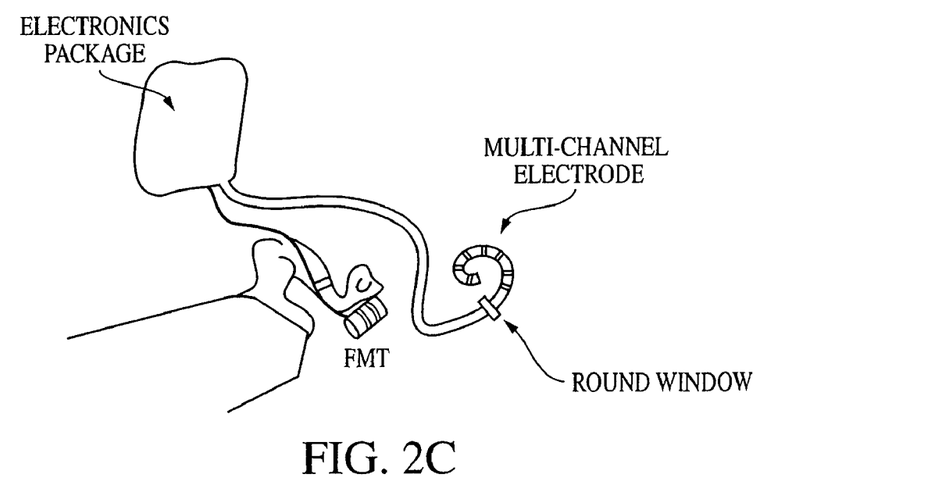
Figure 3A:
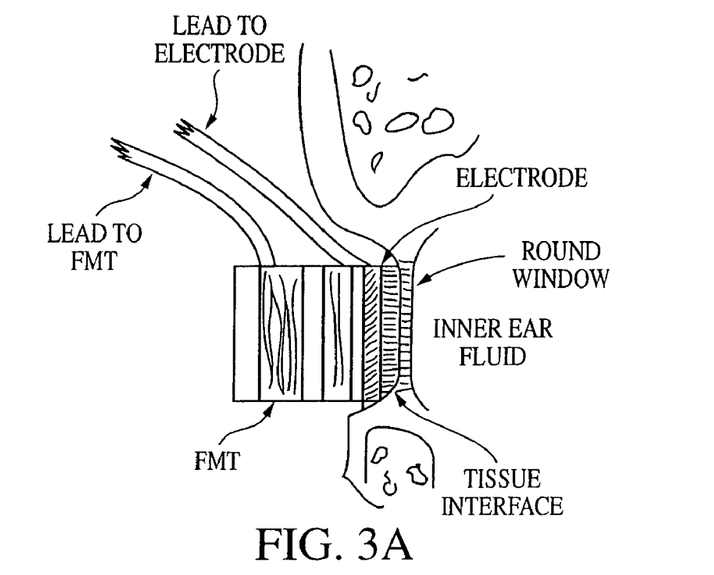
Figure 3B:
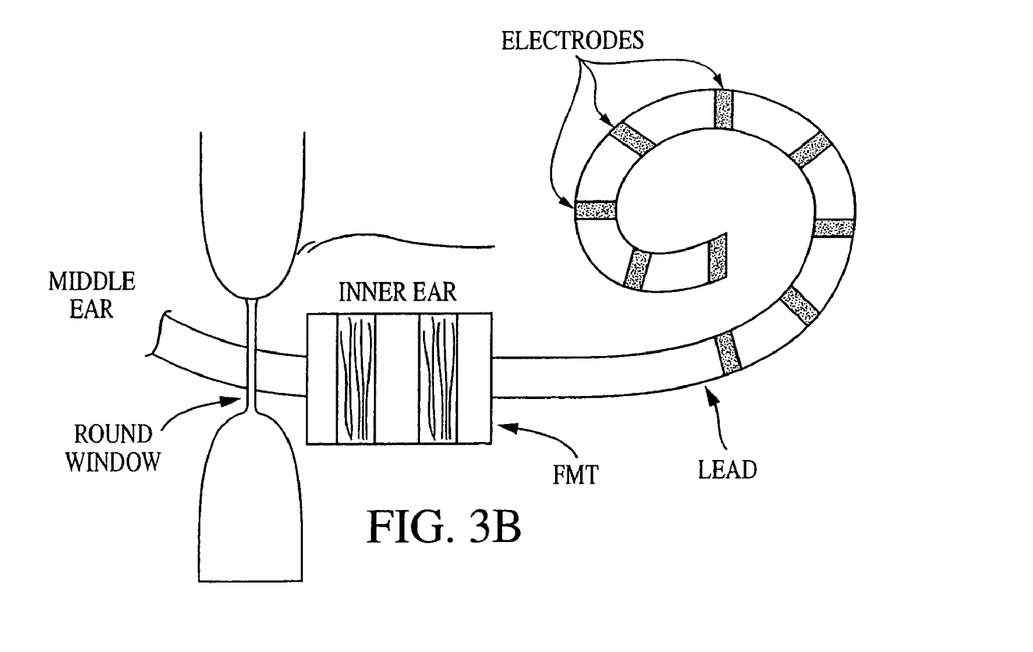

The partially and totally implantable hearing devices of the present invention take a wide variety of forms. In one embodiment as shown in FIG. 2 Panel A, a floating mass transducer is placed on the ossicular chain and an electrode is placed on the round window. The floating mass transducer imparts vibratory motion to the ear, while the electrode stimulates the cochlea electrically. In another embodiment as shown in FIG. 2 Panel B, a floating mass transducer is placed on the ossicular chain and multiple electrodes are placed at different locations around the outside of the cochlea. In a further embodiment as shown in FIG. 2 Panel C, a multi-channel electrode is used in combination with a floating mass transducer and either a means for preventing drainage of the cochlear fluid or a means for replacement of the cochlear fluid. Alternatively, both the floating mass transducer and the electrode are placed together on the round window (See, e.g., FIG. 3 Panel A, device comprising a floating mass transducer with an electrode on the surface facing the round window). Suitable configurations for implantation in the inner ear for stimulation of the cochlear fluid comprise either a floating mass transducer connected to an electrode array, or an electrode connected to multiple floating mass transducers (See, e.g., FIG. 3 Panel B).

Figure 4A:
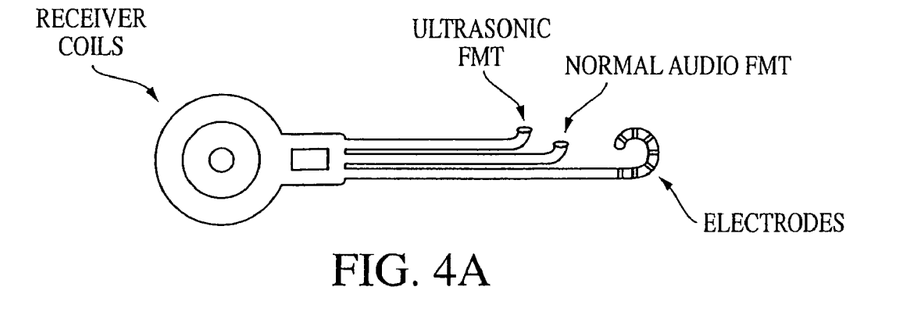
Figure 4B:
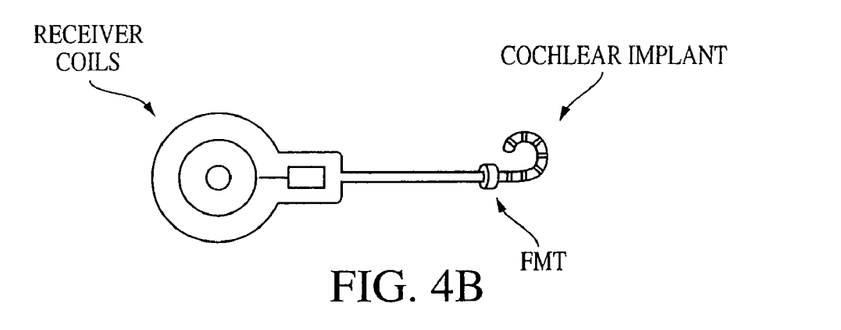
Figure 4C:
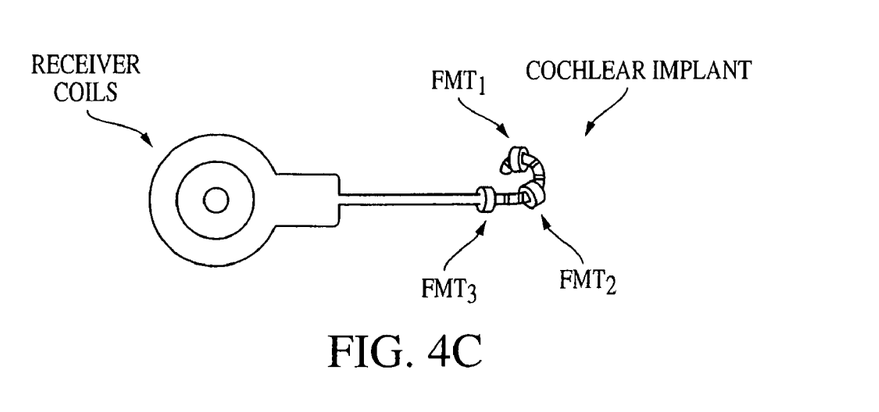

As shown in FIG. 4 Panel A, some embodiments of the implantable hearing devices of the present invention provide mechanical stimulation in the form of both an ultrasonic floating mass transducer, and an audio floating mass transducer in addition to electric stimulation. In this way, a single implant provides multiple stimulation modes for patients with especially troublesome hearing loss.

DEFINITIONS

To facilitate an understanding of the present invention, a number of terms and phrases are defined below:

As used herein, the term "subject" refers to a human or other animal. It is intended that the term encompass patients, such as hearing impaired patients.

The terms "hearing impaired subject" and "hearing impaired patient" refer to animals or persons with any degree of loss of hearing that has an impact on the activities of daily living or that requires special assistance or intervention. Subjects with severe (sound detection above 70 dB) to profound (sound detection above 90 dB) hearing loss are preferred candidates for the hearing devices of the present invention.

Subjects with severe "tinnitus" or "ringing in the ears" are also expected to receive benefit from the hearing devices disclosed herein.

As used herein, the terms "external ear canal" and "external auditory meatus" refer to the opening in the skull through which sound reaches the middle ear. The external ear canal extends to the tympanic membrane (or "eardrum"), although the tympanic membrane itself is considered to be part of the middle ear. The external ear canal is lined with skin and due to its resonant characteristics, provides some amplification of sound traveling through the canal. The "outer ear" includes those parts of the ear that are normally visible (e.g., the auricle or pinna, and the surface portions of the external ear canal).

As used herein, the term "middle ear" refers to the portion of the auditory system that is internal to the tympanic membrane, and including the tympanic membrane, itself. It includes the auditory ossicles (i.e., malleus, incus, and stapes, commonly known as the hammer, anvil, and stirrup) that from a bony chain (e.g., ossicular chain) across the middle ear chamber to conduct and amplify sound waves from the tympanic membrane to the oval window. The ossicles are secured to the walls of the chamber by ligaments. The middle ear is open to the outside environment by means of the eustachian tube.

As used herein, the term "inner ear" refers to the fluid-filled portion of the ear. Waves relayed by the ossicles to the oval window are created in the fluid, pass through the cochlea, and stimulate the delicate hair-like endings of the receptor cells of the auditory nerve. These receptors generate electrochemical signals which are interpreted by the brain as sound.

The term "cochlea" refers to the part of the inner ear that is concerned with hearing. The cochlea is a division of the bony labyrinth located anterior to the vestibule, coiled into the form of a snail shell, and consisting of a spiral canal in the petrous part of the temporal bone.

As used herein, the term "cochlear hair cell" refers to the sound sensing cell of the inner ear, which have modified ciliary structures (e.g., hairs), that enable them to produce an electrical (neural) response to mechanical motion caused by the effect of sound waves on the cochlea. Frequency is detected by the position of the cell in the cochlea and amplitude by the magnitude of the disturbance.

The term "cochlear fluid" refers to the liquid within the cochlea which transmits vibrations to the hair cells.

The terms "round window" and "fenestra of the cochlea" refer to an opening in the medial wall of the middle ear leading into the cochlea.

The term "temporal bone" refers to a large irregular bone situated in the base and side of the skull, consisting of the, squamous, tympanic and petrous. The term "mastoid" refers to the process of the temporal bone behind the ear.

As used herein, the term "amplifier" refers to a device that produces an electrical output that is a function of the corresponding electrical input parameter, and increases the magnitude of the input by means of energy drawn from an external source (i.e., it introduces gain). "Amplification" refers to the reproduction of an electrical signal by an electronic device, usually at an increased intensity. "Amplification means" refers to the use of an amplifier to amplify a signal. It is intended that the amplification means also includes means to process and/or filter the signal.

As used herein, the term "receiver" refers to the part of a system that converts transmitted waves into a desired form of output. The range of frequencies over which a receiver operates with a selected performance (i.e., a known level of sensitivity) is the "bandwidth" of the receiver. The "minimal discernible signal" is the smallest value of input power that results in output by the receiver.

As used herein, the term "transmitter" refers to a device, circuit, or apparatus of a system that is used to transmit an electrical signal to the receiving part of the system. A "transmitter coil" is a device that receives an electrical signal and broadcasts it to a "receiver coil." It is intended that transmitter and receiver coils may be used in conjunction with centering magnets which function to maintain the placement of the coils in a particular position and/or location.

As used herein, the terms "speaker" and "loudspeaker" refer to electroacoustic devices that convert electrical energy into sound energy. The speaker is the final unit in any sound reproducer or acoustic circuit of any broadcast receiver. It is not intended that the present invention be limited to any particular type of speaker. For example, the term encompasses loudspeakers including but not limited to magnetic, cone, horn, crystal, magnetorestriction, magnetic-armature, electrostatic, and labyrinth speakers. It is also intended that multiple speakers of the same or different configurations will be used in the present invention.

As used herein, the term "microphone" refers to a device that converts sound energy into electrical energy. It is the converse of the loudspeaker, although in some devices, the speaker-microphone may be used for both purposes (i.e., a loudspeaker microphone). Various types of microphones are encompassed by this definition, including carbon, capacitor, crystal, moving-coil, and ribbon embodiments. Most microphones operate by converting sound waves into mechanical vibrations that then produce electrical energy. The force exerted by the sound is usually proportional to the sound pressure. In some embodiments, a thin diaphragm is mechanically coupled to a suitable device (e.g., a coil). In alternative embodiments the sound pressure is converted to electrical pressure by direct deformation of suitable magnetorestrictive or piezoelectric crystals (e.g., magnetorestriction and crystal microphones).

The term "circuit" as used herein, refers to the complete path of an electric current.

As used herein, the term "transducer" refers to any device that converts a non-electrical parameter (e.g., sound, pressure or light), into electrical signals or vice versa. Microphones are one type of electroacoustic transducer.

As used herein, the term "resistor" refers to an electronic device that possesses resistance and is selected for this use. It is intended that the term encompass all types of resistors, including but not limited to, fixed-value or adjustable, carbon, wire-wound, and film resistors. The term "resistance" (R; ohm) refers to the tendency of a material to resist the passage of an electric current, and to convert electrical energy into heat energy.

The term "magnet" refers to a body (e.g., iron, steel or alloy) having the property of attracting iron and producing a magnetic field external to itself, and when freely suspended, of pointing to the poles.

As used herein, the term "magnetic field" refers to the area surrounding a magnet in which magnetic forces may be detected.

The term "vibrations" refer to limited reciprocating motions of a particle of an elastic body or medium in alternately opposite directions from its position of equilibrium, when that equilibrium has been disturbed.

The term "coil" refers to an object made of wire wound in a spiral configuration, used in electronic applications.

As used herein, the term "electrode" refers to a conductor used to establish electrical contact with a nonmetallic part of a circuit. In preferred embodiments, the term "electrode"

refers to a conductor used to impart an electric current into a structure of the ear (e.g., round window, cochlea, etc.). The term "microelectrode array" refers to an ordered set of electrodes with extremely small tips, used to stimulate bioelectric potentials of single cells.

The term "leads" refers to wires covered with an insulator used for conducting current between device components (e.g., receiver to transducer or receiver to electrode microarray).

As used herein, the terms "floating mass transducer" and "FMT™" refer to a transducer with a mass that vibrates in direct response to an external signal which corresponds to sound waves. The mass is mechanically coupled to a housing which is mountable on a vibratory structure of the ear. Thus, the mechanical vibration of the floating mass is transformed into a vibration of the vibratory structure allowing the patient to hear. A floating mass transducer can also be utilized as a transducer to transform mechanical vibrations into electrical signals.

As used herein, the term "soundbridge" refers to medical prostheses that serve to improve the hearing of individuals. Although it is not intended that the present invention be so limited, in particularly preferred embodiments, soundbridges are used to improve the hearing of individuals with sensorineural, conductive (i.e., the ossicular connection is broken, loose, stuck, or missing), or mixed sensorineural and conductive hearing loss. Unlike hearing aids that take a sound and make it louder as it enters the middle ear, in particularly preferred embodiments, soundbridges convert acoustic sound to vibrations inside the middle ear. These vibrations are amplified by device electronics in order to make the vibrations stronger than the patient would normally achieve with sound transmitted through the ear canal and across the eardrum. Since in the most preferred embodiments no portion of the soundbridge is present in the ear canal, problems commonly experienced with hearing aids (e.g., occlusion, discomfort, irritation, soreness, feedback, external ear infections, etc.), are eliminated or reduced.

In highly preferred embodiments, the soundbridge is divided into two components, with the external portion comprising an audio processor (e.g., comprised of a microphone, battery, and the electronics needed to convert sound to a signal that can be transmitted to the internal portion of the soundbridge) and the internal portion comprising an internal receiving link and a floating mass transducer (FMT™). The audio processor is positioned on the wearer's head with a magnet. A signal from the audio processor is transmitted across the skin to an internal receiver, which then relays the signal via a conductor link to the FMT™. In turn, the FMT™ converts the signal to vibrations that move the bones of the middle ear in a manner similar to the way in which sounds move them. Thus, ambient sounds (e.g., voices, etc.) are picked up by the microphone in the audio processor and converted to an electrical signal within the audio processor. This electrical signal is then transmitted across the skin to the internal receiver which then conveys the signal to the FMT™ via a conducting link, resulting in mechanical vibration of the ossicles, which are then interpreted by the wearer.

As used herein, the term "battery" refers to a cell that furnishes electric current to the hearing devices of the present invention. In preferred embodiments of the present invention, "rechargeable" batteries are used.

In other preferred embodiments, the present invention provides a completely implantable system in which the microphone, battery, and electronics are positioned under the patient's skin. In such embodiments, the battery is positioned and designed so as to allow recharging while the battery is implanted (i.e., the battery is recharged while it is in position in situ).

The term "housing" refers to the structure encasing or enclosing at least one component (e.g., microphone, battery, electronics, transducer, etc.) of the devices of the present invention. In preferred embodiments, the "housing" is produced from a "biocompatible" material. In particularly preferred embodiments, the housing comprises at least one hermetic feedthrough through which leads extend from the component inside the housing to a position outside the housing.

As used herein, the term "biocompatible" refers to any substance or compound that has minimal (i.e., no significant difference is seen compared to a control) to no irritant or immunological effect on the surrounding tissue. It is also intended that the term be applied in reference to the substances or compounds utilized in order to minimize or to avoid an immunologic reaction to the housing or other aspects of the invention. Particularly preferred biocompatible materials include, but are not limited to titanium, gold, platinum, sapphire, and ceramics.

As used herein, the term "implantable" refers to any device that may be surgically implanted in a patient. It is intended that the term encompass various types of implants. In preferred embodiments, the device may be implanted under the skin (i.e., subcutaneous), or placed at any other location suited for the use of the device (e.g., within temporal bone, middle ear or inner ear). An implanted device is one that has been implanted within a subject, while a device that is "external" to the subject is not implanted within the subject (i.e., the device is located externally to the subject's skin). Similarly, the term "surgically implanting" refers to the medical procedure whereby the hearing device is placed within a living body.

As used herein, the term "hermetically sealed" refers to a device or object that is sealed in a manner that liquids or gases located outside the device are prevented from entering the interior of the device, to at least some degree. "Completely hermetically sealed" refers to a device or object that is sealed in a manner such that no detectable liquid or gas located outside the device enters the interior of the device. It is intended that the sealing be accomplished by a variety of means, including but not limited to mechanical, glue or sealants, etc. In particularly preferred embodiments, the hermetically sealed device is made so that it is completely leak-proof (i.e., no liquid or gas is allowed to enter the interior of the device at all).

As used herein, the term "reproduction of sound" refers to the reproduction of sound information from an audiofrequency source of electrical signals. It is intended that the term encompass complete sound reproduction systems (i.e., comprising the original source of audio information, preamplifier, and control circuits, audiofrequency power amplifier[s] and loudspeaker[s]). It is intended that the term encompass monophonic, as well as stereophonic sound reproduction, including stereophonic broadcast transmission. In some embodiments, a sound reproduction system composed of high-quality components, and which reproduces the original audio information faithfully and with very low noise levels, is referred to as a "high-fidelity" system (hi-fi). As used herein, the term "audio processor" refers to any device or component that processes sound for any purpose.

As used herein, the term "acoustic wave" and "sound wave" refer to a wave that is transmitted through a solid, liquid, and/or gaseous material as a result of the mechanical vibrations of the particles forming the material. The normal mode of wave propagation is longitudinal (i.e., the direction of motion of the particles is parallel to the direction of wave propagation), the wave therefore consists of compressions and rarefactions of the material. It is intended that the present invention encompass waves with various frequencies, although waves falling within the audible range of the human ear (e.g., approximately 20 Hz to 20 kHz) are particularly preferred. Waves with frequencies greater than approximately 20 kHz are "ultrasonic" waves.

As used herein, the term "frequency" (v or f) refers to the number of complete cycles of a periodic quantity occurring in a unit of time. The unit of frequency is the "hertz," corresponding to the frequency of a periodic phenomenon that has a period of one second. Table 1 below lists various ranges of frequencies that form part of a larger continuous series of frequencies. Internationally agreed radiofrequency bands are shown in this table. Microwave frequencies ranging from VHF to EHF bands (i.e., 0.225 to 100 GHz) are usually subdivided into bands designated by the letters, P, L, S, X, K, Q, V, and W.

TABLE 1

Radiofrequency Bands

| Frequency | Band | Wavelength |
| --- | --- | --- |
| 300 to 30 GHz | Extremely High Frequency (EHF) | 1 mm to 1 cm |
| 30 to 3 GHz | Superhigh Frequency (SHF) | 1 cm to 10 cm |
| 3 to 0.3 GHz | Ultrahigh Frequency (UHF) | 10 cm to 1 m |
| 300 to 30 MHz | Very High Frequency (VHF) | 1 m to 10 m |
| 30 to 3 MHz | High Frequency (HF) | 10 m to 100 m |
| 3 to 0.3 MHz | Medium Frequency (MF) | 100 m to 1000 m |
| 300 to 30 kHz | Low Frequency (LF) | 1 km to 10 km |
| 30 to 3 kHz | Very Low Frequency (VLF) | 10 km to 100 km |

As used herein, the term "gain," measured in decibels, is used as a measure of the ability of an electronic circuit, device, or apparatus to increase the magnitude of a given electrical input parameter. In a power amplifier, the gain is the ratio of the power output to the power input of the amplifier. "Gain control" (or "volume control") is a circuit or device that varies the amplitude of the output signal from an amplifier.

As used herein, the term "decibel" (dB) is a dimensionless unit used to express the ratio of two powers, voltages, currents, or sound intensities. It is 10× the common logarithm of the power ratio. If two power values (P1 and P2) differ by n decibels, then $n=10 \log_{10}(P2/P1)$, or $P2/P1=10^{n/10}$. If P1 and P2 are the input and output powers, respectively, of an electric network, if n is positive (i.e., P2>P1), there is a gain in power. If n is negative (i.e., P1>P2), there is a power loss.

As used herein, the terms "carrier wave" and "carrier" refer to a wave that is intended to be modulated by a signal that is to be transmitted. The process of modulation produces spectral components termed "sidebands" that fall into frequency bands at either the upper ("upper sideband") or lower ("lower sideband") side of the carrier frequency. A sideband in which some of the spectral components are greatly attenuated is referred to a "vestigial sideband." Generally, these components correspond to the highest frequency in the modulating signals. A single frequency in a sideband is referred to as a "side frequency," while the "baseband" is the frequency band occupied by all of the transmitted modulating signals.

The term "modulation" is used in general reference, to the alteration or modification of any electronic parameter by another. For example, it encompasses the process by which certain characteristics of one wave (the "carrier wave" or "carrier signal") are modulated or modified in accordance with the characteristic of another wave (the "modulating wave"). The reverse process is "demodulation," in which an output wave is obtained that has the characteristics of the original modulating wave or signal. Characteristics of the carrier that may be modulated include the amplitude, and phase angle. Modulation by an undesirable signal is referred to as "cross modulation," while "multiple modulation" is a succession of processes of modulation in which the whole, or part of the modulated wave from one process becomes the modulating wave for the next.

As used herein, the term "demodulator" ("detector") refers to a circuit, apparatus, or circuit element that demodulates the received signal (i.e., extracts the signal from a carrier, with minimum distortion). "A modulator" is any device that effects modulation.

As used herein, the term "dielectric" refers to a solid, liquid, or gaseous material that can sustain an electric field and act as an insulator (i.e., a material that is used to prevent the loss of electric charge or current from a conductor, insulators have a very high resistance to electric current, so that the current flow through the material is usually negligible).

As used herein, the term "electronic device" refers to a device or object that utilizes the properties of electrons or ions moving in a vacuum, gas, or semiconductor. "Electronic circuitry" refers to the path of electron or ion movement, as well as the direction provided by the device or object to the electrons or ions. A "circuit" or "electronics package" is a combination of a number of electrical devices and conductors that when connected together, form a conducting path to fulfill a desired function, such as amplification, filtering, or oscillation. Any constituent part of the circuit other than the interconnections is referred to as a "circuit element." A circuit may be comprised of discrete components, or it may be an "integrated circuit." A circuit is said to be "closed," when it forms a continuous path for current. It is contemplated that any number of devices be included within an electronics package. It is further intended that various components be included in multiple electronics packages that work cooperatively to amplify sound. In some embodiments, the "vocal electronics" package refers to the entire system used to improve and/or amplify sound production.

As used herein, the term "electret" refers to a substance that is permanently electrified, and has oppositely charged extremities.

As used herein, the term "reset" refers to the restoration of an electrical or electronic device or apparatus to its original state following operation of the equipment.

As used herein, the term "residual charge" refers to the portion of a charge stored in a capacitor that is retained when the capacitor is rapidly discharged, and may be subsequently withdrawn. Although it is not necessary to understand the mechanism to use the present invention, and the present invention present invention is not limited to any particular mechanism of action, it is hypothesized that this results from viscous movement of the dielectric under charge causing some of the charge to penetrate the dielectric and therefore, become relatively remote from the plates; only the charge near the plates is removed by rapid discharge.

As used herein, the term "current" refers to the rate of flow of electricity. The current is usually expressed in amperes; the symbol used is "I."

As used herein, the term "residual current" refers to a current that flows for a short time in the external circuit of an active electronic device after the power supply to the device has been turned off. The residual current results from the finite velocity of the charge carriers passing through the device. The term "active" is used in reference to any device, component or circuit that introduces gain or has a directional function. An "active current," "active component," energy component," "power component" or "in-phase component of the current" refers to the component that is in phase with the voltage, alternative current, and voltage being regarded as vector quantities. The term "passive" refers to any device, component or circuit that does not introduce gain, or does not have a directional function. It is intended that the term encompass pure resistance, capacitance, inductance, or a combination of these.

As used herein, the terms "power source" and "power supply" refer to any source of electrical power in a form that is suitable for operating electronic circuits. Alternating current power may be derived either directly or by means of a suitable transformer. "Alternating current" refers to an electric current whose direction in the circuit is periodically reversed with a frequency f, that is independent of the circuit constants. Direct current power may be supplied from various sources, including, but not limited to batteries, suitable rectifier/filter circuits, or from a converter. "Direct current" refers to an unidirectional current of substantially constant value. The term also encompasses embodiments that include a "bus" to supply power to several circuits or to several different points in one circuit. A "power pack" is used in reference to a device that converts power from an alternating current or direct current supply, into a form that is suitable for operating electronic device(s).

The term "piezoelectric effect" refers to the property of certain crystalline or ceramic materials to emit electricity when deformed and to deform when an electric current is passed across them, a mechanism of interconverting electrical and acoustic energy; an ultrasound transducer sends and receives acoustic energy using this effect.

The term "cochlear implant" refers to an electronic device implanted under the skin with electrodes in the middle ear on the promontory or cochlear window or in the inner ear in the cochlea to create sound sensation in total sensory deafness. A microphone behind the ear feeds sound waves into a microprocessor carried on the body, which analyzes the data and sends information back to a radio transmitter that triggers the electrodes in the middle or inner ear to produce the appropriate electrical pulses. This does not enable the patient actually to hear, but rather to distinguish different sounds according to the neural sensation they produce.

As used herein, the term "electronics" refers to a conductor used to make electrical contact with some part of a circuit.

The term "ominidirectional microphone" as used herein refers to a microphone that picks up sound at essentially equal levels in all directions. The coverage pattern is essentially 360-degrees with essentially no angle of rejection. In contrast, the term "bidirectional microphone" refers to a microphone that picks up sound essentially equally from two directions. This type of microphone picks up sound from two directions and largely rejects sound from the sides.

As used herein, the term "channel" refers to a circuit or signal path within a piece of equipment. For example, in a mixer it refers to an input channel (all of the controls and circuitry that affects a single microphone or line-level device), or an output channel (all of the controls and circuitry that affects a single output).

The term "resonant frequency" as used herein refers to the frequency at which a piezoelectric ceramic will vibrate most efficiently (will produce the highest output with the least amount of voltage applied). The term "resonance" refers to a natural periodicity, or the reinforcement associated with this periodicity.

As used herein the term "block" refers to a number or quantity of related components dealt with as a single unit.

The term "signal" refers to an electrical current present on a wire or in a circuit that represents a soundwave.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A device for improving hearing in a subject, comprising:
    a) a receiver;
    b) an array of electrical transducers;
    c) a single mechanical transducer; and
    d) a single output channel lead with a proximal end operably connected to said receiver, wherein said single output channel lead comprises a wire configured for conducting current, wherein said electrical transducer and said mechanical transducer are connected in series along said single output channel lead, wherein said single output channel lead is connected to only one mechanical transducer, that being said single mechanical transducer, and wherein all of the electrical transducers in said array of electrical tranducers that are connected to said single output channel lead are distal to said single mechanical transducer and are configured for implanting in a subject's cochlea.

2. The device of claim 1, wherein said receiver is configured for implantation within said subject's mastoid bone.

3. The device of claim 1, wherein said mechanical transducer comprises a floating mass transducer.

4. The device of claim 1, wherein said mechanical transducer has a resonant frequency between 250 and 10,000 hertz.

* * * * *

UNITED STATES PATENT AND TRADEMARK OFFICE
CERTIFICATE OF CORRECTION

| | | |
|---|---|---|
| PATENT NO. | : 8,285,384 B2 | Page 1 of 1 |
| APPLICATION NO. | : 11/654917 | |
| DATED | : October 9, 2012 | |
| INVENTOR(S) | : Ball et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this
Twenty-ninth Day of December, 2015

Michelle K. Lee
*Director of the United States Patent and Trademark Office*